United States Patent [19]
Kranbuehl

[11] Patent Number: 5,317,252
[45] Date of Patent: May 31, 1994

[54] DOSIMETER FOR MONITORING THE CONDITION OF POLYMERIC MATERIALS AND CHEMICAL FLUIDS

[76] Inventor: David E. Kranbuehl, 201 Harrison Ave., Williamsburg, Va. 23185

[21] Appl. No.: 944,928

[22] Filed: Sep. 15, 1992

[51] Int. Cl.⁵ ............................................. G01N 27/00
[52] U.S. Cl. .................................. 324/71.7; 324/681; 324/686; 324/690
[58] Field of Search .................. 324/71.1, 658, 663, 324/674, 681, 686, 690, 693, 707; 422/82.01

[56] References Cited

U.S. PATENT DOCUMENTS

| | | | |
|---|---|---|---|
| 4,370,611 | 1/1983 | Gregory et. al. | 314/674 X |
| 4,710,550 | 12/1987 | Kranbuehl | 324/690 X |
| 4,723,908 | 2/1988 | Kranbuehl | 324/687 X |
| 5,045,798 | 9/1991 | Hendrick | 324/690 X |
| 5,184,077 | 2/1993 | Day et al. | 324/693 |
| 5,208,544 | 5/1993 | McBrearty et al. | 324/690 X |
| 5,219,498 | 6/1993 | Keller et al. | 324/663 X |

OTHER PUBLICATIONS

Zaretsky et al; "Estimation of Thickness, Complex Bulk Permittivity and Surface Conductivity Using Interdigital Dielectrometry"; IEEE Transactions on Electrical Insulation; vol. 24, #6, Dec. 1989; pp. 1159–1166.

Primary Examiner—Kenneth A. Wieder
Assistant Examiner—Chris Tobin
Attorney, Agent, or Firm—Whitham & Marhoefer

[57] ABSTRACT

A dosimeter with reproducible changes in $\epsilon'$, $\epsilon''$, or their equivalent two parameter circuit representations, under a given treatment regime that correlate directly with changes in physical attributes of a material or fluid, such as strength, modulus or viscosity, is used to monitor the deterioration of the physical attributes of the material or fluid.

11 Claims, 2 Drawing Sheets

DOSIMETER FOR MONITORING THE CONDITION OF POLYMERIC MATERIALS AND CHEMICAL FLUIDS

BACKGROUND OF THE INVENTION

1. Field of the Invention

The invention is generally related to monitoring the condition of a polymeric material or a chemical fluid using a frequency dependent electromagnetic sensor. More particularly, the invention is directed to a dosimeter device which has reproducible electrical permittivity characteristics for a given treatment history that are matched to physical attribute characteristics of a polymeric material or chemical fluid being monitored, whereby the deterioration of the physical attributes of the polymeric material or chemical fluid can be discerned from a permittivity measurement, real and/or imaginary component, of the dosimeter.

2. Description of the Prior Art

U.S. Pat. Nos. 4,710,550 and 4,723,908 to Kranbuehl, both of which are herein incorporated by reference, describe a probe and its method of use in monitoring the changing processing properties of a polymeric resin as it is fabricated into a part in an oven, press, or autoclave. The probe is preferably thin and flat, and includes an array of electrode lines in an interdigitated pectinate configuration on a substrate. The lines are made of a conductive material, such as tungsten, gold, copper, platinum, palladium, chromium, or alloys of the same. The lines on the Kranbuehl probe are less than 10 mils (one thousandth of an inch) apart, less than 20 mils wide, and form the two terminals of a capacitor. The substrate in the Kranbuehl probe has a low loss tangent over a frequency range of one Hertz (Hz) to approximately 10 megaHz. In particular, the substrate has a conductivity which remains below approximately $10^{-7} \text{ohm}^{-1}\text{cm}^{-1}$ over its range of use, which in thermal processing of polymers can range between 0° C. to 500° C. Exemplary substrates include $A_2O_3$, glass, ceramic, and low loss polymer film (e.g., Kapton ®).

In operation, a material is placed on the substrate in contact with the array of lines. A voltage is placed across the two electrically isolated arrays. An electric field between the lines passes up and through the material which is in contact with the probe. Hence, the probe utilizes the fringing effects of the electric field to measure the dielectric properties of the material, as well as the electric field which passes through the small amount of material which is directly between the lines. Measurements are preferably made with an impedance analyzer which includes low noise, automatic bridges that can span up to six decades or more in frequency. The impedance analyzer measures the opposition that a material presents to an alternating current in terms of the complex ratio of the voltage to the current. This relationship is set forth in Equation 1

$$Z^* = V(\omega)/I(\omega) \qquad \text{Eq. 1}$$

where $Z^*$ is the complex impedance. The output of the impedance analyzer is representative of the magnitude and time shift of the voltage relative to the current.

The Kranbuehl patents discuss in detail how the properties of the material can be represented as an equivalent circuit of a resistor and a capacitor in parallel and how the material's electrical properties acquired using the impedance analyzer are best understood in terms of its complex permittivity ($\epsilon^*$), an intensive property of the material which has both real and imaginary components. Equation 2 presents the complex permittivity calculation.

$$\epsilon^* = \epsilon' - i\epsilon'' \qquad \text{Eq. 2}$$

The complex impedance sensed by the impedance analyzer can be modeled as a parallel circuit which includes both a resistor and a capacitor. As explained in the Kranbuehl patents, measurements of the equivalent parallel circuit components of the complex impedance, e.g., the capacitance C and the conductance G, are used to calculate $\epsilon^*$. Using either bridge or time-domain techniques, the real and imaginary components of the material's macroscopic impedance $Z^*$ is determined as a function of frequency. The complex permittivity $\epsilon^*$ can be calculated knowing the capacitance of the material ($C_p$), the capacitance of the probe without the material ($C_o$), and the conductance of the material ($G_p$) as set forth below in Equations 3 and 4.

$$\epsilon' = C_p/C_o \qquad \text{Eq. 3}$$

$$\epsilon'' = G_p/\omega C_o \qquad \text{Eq. 4}$$

Both the real and imaginary components of $\epsilon^*$ have dipolar and ionic components as indicated by Equations 5 and 6.

$$\epsilon' = \epsilon'd + \epsilon'i \qquad \text{Eq. 5}$$

$$\epsilon'' = \epsilon''d + \epsilon''i \qquad \text{Eq. 6}$$

Understanding the contribution of the dipolar mobility and ionic mobility components can provide an understanding of the physical nature of the material being analyzed.

Kranbuehl et al., *Am. Chem. Soc., Los Angeles Meeting, Polymeric Materials Science and Engineering Division*, Sept. 1988, pp. 839–843, reported that the frequency dependent output of electromagnetic sensors (FDEMS), like those discussed in the Kranbuehl patents, can be used in life monitoring, whereby output could be used to discern the molecular state of composite and polymeric structures as they physically change during use due to extended exposure to chemicals, stress-strain extremes, temperature extremes, high energy radiation, and atomic oxygen. On a molecular level these environmental effects change the chemical structure, cross-link network and morphology of the polymer, which, in turn, changes the structure's toughness, strength and point of failure. It was particularly observed that the real component of permittivity, $\epsilon'$, remained stable for a short period of time at an elevated temperature and then declined rapidly. This indicates that the complex permittivity measurements made with the Kranbuehl probes could be used as a qualitative indicator of thermal degradation of a material.

SUMMARY OF THE INVENTION

It is an object of this invention to provide a dosimeter for monitoring the deterioration of the physical properties of a polymeric material or chemical fluid.

According to the invention, a dosimeter is constructed from a substrate with an interdigitated electrode pattern forming a capacitor thereon or other equivalent capacitor configuration. The substrate, the thickness of the substrate, the electrode pattern, the spacing between the digits of the electrode pattern, and the like, are closely controlled and are optimized to provide a dosimeter with reproducible changes in $\epsilon'$ and $\epsilon''$, or equivalent circuit representations thereof, under a given treatment regime. The dosimeter is fabricated such that the changes in $\epsilon'$ and/or $\epsilon''$ correlate directly with changes in physical attributes of a material or fluid.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1A:
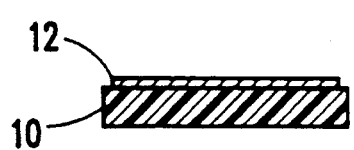
FIGS. 1a-d are cross-sectional side views of dosimeters showing different substrate configurations which may be used within the practice of this invention.

Many materials and fluids are expected to perform under harsh environmental conditions during their useful life. For example, polymeric materials and composites have been used in aerospace applications where they are exposed to extreme temperature, stress/strain conditions, liquids and/or gases which cause deterioration, as well as intense doses of radiation including ultraviolet (UV) and visible (vis) radiation, etc. Extreme conditions and radiation can cause scission of the polymer chains, which can degrade toughness and strength of the polymeric materials and composites. Oils, greases and other viscous fluids are often used in high temperature applications which can break down the viscosity of these fluids, thereby limiting the lubricating properties of the fluids. Adhesives and caulks are often exposed to corrosive chemicals which can either breakdown the polymeric structure of the adhesive or cause embrittlement, a reaction which crosslinks the chains while reducing the beneficial rubber-like properties of the adhesives and caulks.

The complex permittivity $\epsilon^*$ can be used as an indicator of the molecular integrity and structure of polymeric materials and chemical fluids. For example, when a polymeric material or composite experiences chain scission due to thermal temperatures or intense stress/strain conditions breaking bonds in the polymer backbone, the dipolar and ionic mobility contribution, $\epsilon'd$, $\epsilon'i$, $\epsilon''d$, and $\epsilon''i$, to the complex permittivity will increase. Conversely, if a material moves towards a state of embrittlement where crosslinked polymer chains are formed, the dipolar and ionic components of the complex permittivity will often decrease.

This invention is particularly related to providing a dosimeter which has significant, reproducible changes in its real component or permittivity, $\epsilon'$, and/or its imaginary component or loss parameter, $\epsilon''$, or any of the equivalent two parameter impedance representations such as an equivalent parallel capacitor/resistor circuit, i.e., R,C; G,X; $|z|$, $\theta$; C,D; etc., with the cumulative effect of the level and time of exposure of the dosimeter in a hostile environment (e.g., high temperature, high stress/strain, harsh liquids or gases, intense radiation exposure, etc.). The dosimeter is designed such that changes in $\epsilon'$, $\epsilon''$ or equivalent circuit representations thereof correspond with changes in a "use property" or "physical attribute" of a polymeric material or chemical fluid to be monitored, such as a strength or modulus of a polymeric material or composite or viscosity of a chemical fluid. Preferably, the extent of the desired change in $\epsilon'$ and/or $\epsilon''$ for extent the dosimeter with exposure history is matched to correlate with a change in the use property or physical attribute of the polymeric material or chemical fluid from an initial value to a value where attention is required. For example, an initial $\epsilon'$ and/or $\epsilon''$ value measured by the dosimeter would correspond with a polymeric material in a structure or part which has not been exposed to extreme temperature conditions, and an ending $\epsilon'$ and/or $\epsilon''$ value would correspond to a level of degradation in the polymeric material where the structure or part should be replaced or serviced.

Figure 5:
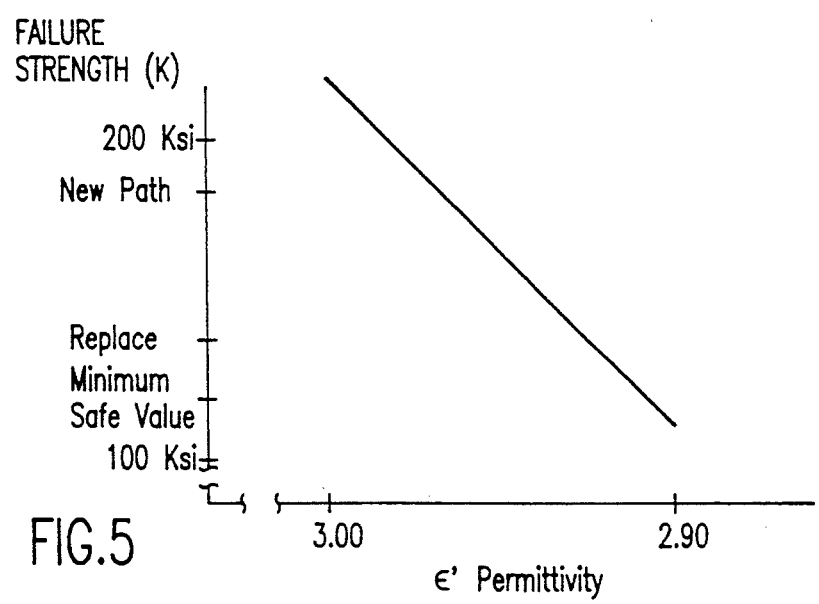
FIG. 5 is a graph showing the relationship of the failure strength, K, of a material and the decline in the permittivity, $\epsilon'$, of a dosimeter.

In summary, the dosimeter, through selection and design of the material and electrode pattern, produces a functional variation in $\epsilon'$ and/or $\epsilon''$ which is measurable for changes in the value of concern (e.g., modulus (m), strength (k), viscosity, etc.). For example, FIG. 5 shows the decline in the permittivity, $\epsilon'$, correlated with drop in failure strength, k, of a polymer composite. The ability of measurements of $\epsilon'$, $\epsilon''$, or their two parameter circuit equivalent representations thereof, to be correlated with use properties of concern such as viscosity, weight loss, crystallinity, softening temperature, Tg, and fraction of unreacted reactive groups is reported in the literature (see, Kranbuehl, *International Encyclopedia of Composites*, VCH Publishers, ed. Lee, Vol. 1, pp. 531-543 (1990)). Mechanical properties, such as failure strength or flexure modulus, etc., are similarly related to circuit structure (see, N. McCrum, B. Read, G. Williams, *Anelastic and Dielectric Effects in Polymeric Solids*, John Wiley & Sons, London, 19671, and Ferry, *Viscoelastic Properties of Polymers*, John Wiley & Sons, New York, 1970) and, thus, can be monitored by measurement of $\epsilon'$ and/or $\epsilon''$ or their equivalent two component representations (e.g., R,C; G,X; $|z|$,$\theta$; C,D; etc.). FIG. 5 shows that a dosimeter can be designed to provide reproducible changes in $\epsilon'$ and/or $\epsilon''$ which are a function of modulus ($\epsilon'$=f(m)) of a part being monitored in an adverse environment over an extended period of exposure.

Unlike the previously described sensor probes in U.S. Pat. Nos. 4,710,550 and 4,723,908 to Kranbuehl where particular electrical properties of the substrate (e.g., as low a loss value, $\epsilon''$, as possible, and minimal change in $\epsilon'$ and $\epsilon''$ with the temperature process range, which, for polymers can be from 25° C. to 450° C.) and the electrode configuration (e.g., electrodes spaces less than 10 mils apart) were tightly controlled so that the contribution to impedance by the substrate was negligible so that the changes in $\epsilon'$ and/or $\epsilon''$ observed under processing conditions would be reflecting principally the properties of the material positioned on the substrate, not the probe; this invention focuses on the design of a dosimeter sensor to have large, significant and reproducible changes in $\epsilon'$ and/or $\epsilon''$. The dosimeter substrate, electrode pattern, and geometry are selected and matched to produce a direct correlation, preferably linear, with the change in "use properties" or physical attributes of materials or chemical fluids subjected to harsh environments. Hence, for example, the values of $\epsilon'$ and/or $\epsilon''$ of the dosimeter sensor are designed to change so that the changes correspond with values for the strength (K) or modulus (M) for a material at points of concern throughout a range of exposure conditions that a structure or part made from the material is likely to experience throughout its lifetime. Therefore, by monitoring $\epsilon'$ and/or $\epsilon''$, and equivalent circuit representations thereof, values for a dosimeter which has been exposed to the same conditions that a structure or part made from the material to which the dosimeter is matched, the state of the structure or part can readily be determined. This is accomplished by the design of the sensor and developing a calibration curve which relates the changing $\epsilon'$ and/or $\epsilon''$, or equivalent circuit representations thereof, values for the dosimeter to physical attributes of interest for particular polymeric materials or composites or chemical fluids, as is shown, for example, in FIG. 5.

To achieve maximum sensitivity, accuracy, and reproducibility, the surface area and thickness of the dosimeter substrate could be varied so that the degree of change in the substrate values of $\epsilon'$ and $\epsilon''$, as governed on a molecular level by changes in dipolar and ionic mobility properties, at a particular depth in the substrate is matched so that it changes with the time of exposure similar to that of the use property of interest (e.g., strength, modulus, viscosity, etc.) as it is knocked down through degradation to values of interest and concern. Thus, if accurate monitoring is required over extended periods, both the selection of the substrate material and/or its thickness would be varied to achieve a high degree of sensitivity at many points over an extended exposure time period. Similarly, the electrode pattern, and particularly the spacing between interdigitated electrodes, the electrode widths, or the spacing between parallel surfaces, would be varied and matched so that the time of occurrence of significant degradation in the dosimeter substrate would correspond to the time of occurrence of significant degradation in a polymeric structure's use properties of concern. Ultimately, the selection of the substrate, its thickness, the electrode pattern, and the electrode spacing are matched to achieve optimum sensitivity, accuracy and reproducibility in the variation of $\epsilon'$ and/or $\epsilon''$ or their equivalent circuit representations with cumulative exposure level integrated over time.

In many cases, this results in the selection of a specific dosimeter substrate, a specific thickness, and a specific electrode geometry with controlled interdigitated electrode spacing. FIGS. 1a–d show alternative configurations for dosimeters within the practice of this invention. FIG. 1a shows a substrate 10 with an electrode pattern 12 thereon. As explained above, the choice of substrate 10 material influences the magnitude and/or frequency dependence of $\epsilon'$, $\epsilon''$, and their equivalent circuit representations, should therefore be matched to the use properties of the material being monitored. The substrate 10 could be a thermoset, such as epoxies, polyamides, bismaleimides, and polyimides, or a thermoplastic, such as polyethers, polysulfones, and hydrocarbon derivatives of ethylene (e.g., vinyls such as polyvinyl chloride, polypropylene, polystyrine, polymethylmethacrylate, polytetrafluoride, etc.). Table 1 indicates representative dosimeter substrates which would be suitable for different temperature ranges of use.

TABLE 1

| Representative Substrate | Temperature Range of Use |
| --- | --- |
| Epoxies | 0–250° C. |
| Polyimides | 250–400° C. |
| Polyamides | 0–200° C. |

Figure 1C:
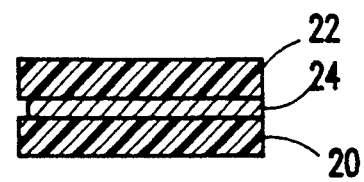
Figure 1B:
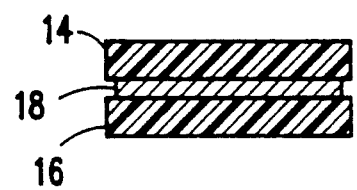
Figure 1D:
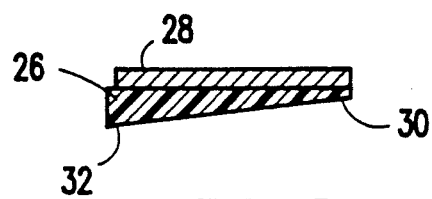

Other substrate materials, such as polyethylene, polyvinylchloride, polyesters, etc., may be selected for their UV-visible radiation degradation properties for limited and long term exposure. Thus, the material, electrode pattern, and geometric design would be selected based on factors such as the type of degradative environment and the exposure time. FIG. 1b shows two different substrates 14 and 16 positioned on either side of the electrode pattern 18. In this case, the fringing field of the electrode pattern 18 will pass through both substrates 14 and 16. By judiciously combining different substrates 14 and 16, a dosimeter with reproducible changes in $\epsilon'$, $\epsilon''$, and their equivalent circuit representations, which correspond directly with use property degradation in a material or chemical fluid to be monitored can be achieved. FIG. 1c shows a dosimeter that is similar in construction to that shown in FIG. 1b, however, here an inert substrate 20 which has little change in $\epsilon'$ and/or $\epsilon''$ is positioned opposite a substrate 22 that has a reproducible change in $\epsilon'$ and/or $\epsilon''$. The Al$_2$O$_3$ and glass substrates described in U.S. Pat. Nos. 4,710,550 and 4,723,908 to Kranbuehl have very little effect on $\epsilon'$ and/or $\epsilon''$ at temperatures ranging from 25°–500° C. and would be suitable as the inert substrate 20. FIG. 1d shows a variation of the dosimeter where the substrate 26 is tapered relative to the electrode pattern 28. As explained above, the thickness of the substrate influences the magnitude and/or frequency dependence of $\epsilon'$, $\epsilon''$, and their equivalent circuit representations. Furthermore, most materials degrade from the exposed surface down. By varying the thickness of the substrate 26 with a tapered region, the deterioration in physical attributes of a structure or part may be monitored over longer periods of time. For example, end 30 deteriorates more rapidly than end 32, however, the magnitude and/or frequency dependence of $\epsilon'$, $\epsilon''$, and their equivalent circuit representations, for the dosimeter of FIG. 1d will be a function of the fringing signals at both ends 30 and 32. In this way, the progression of surface charring in a structure or part towards a point where the integrity of the structure or part is in jeopardy can be monitored. This is important because many times an inspection of the surface of a part will not provide a clear indication of whether the part needs to be replaced. For example, a surface charred part may have a very long useful life ahead of it, while other parts that look identical may be thermally degraded to a point where their useful life has ended.

Figure 2A:
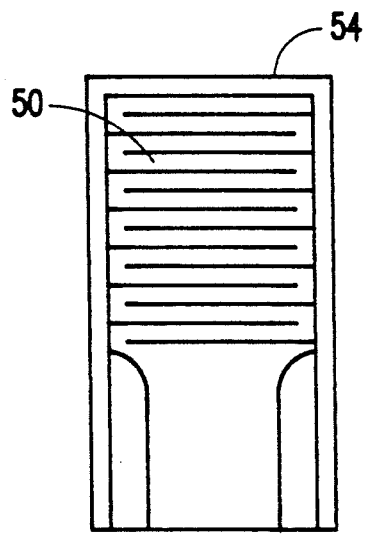
FIGS. 2a-b are top views of different electrode arrangements which can be used on dosimeters within the practice of this invention.
Figure 2B:
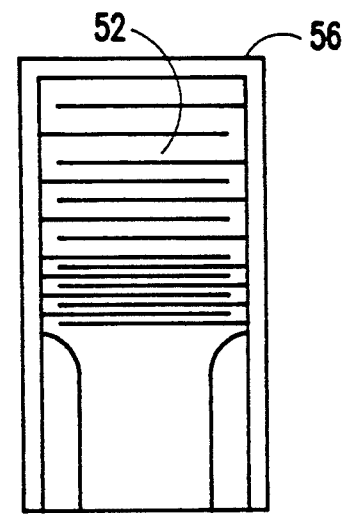

FIGS. 2a and 2b show alternative electrode patterns 50 and 52 on substrates 54 and 56, respectively. As explained above, the spacing and thickness of the electrode patterns can play a significant role in influencing the magnitude and/or frequency dependence of $\epsilon'$, $\epsilon''$, and their equivalent circuit representations. This can be understood simply by noting that the larger distances between lines result in bigger fringing fields between the electrodes and have a deeper radius of penetration. FIG. 2a shows an electrode pattern which is uniform and can have a spacing between lines of less than 10 mils, as is described in U.S. Pat. Nos. 4,710,550 and 4,723,908 to Kranbuehl; however, the spacing could be larger and is dependent on providing a dosimeter with an accurate, reproducible change in the magnitude and/or frequency dependence of $\epsilon'$ and/or $\epsilon''$ that is matched to the use property or physical attribute of the polymeric material or chemical fluid being monitored. FIG. 2b shows the electrode pattern becoming progressively narrower. This design is especially useful for long term monitoring since the radius of the fringing fields between the electrodes will extend to different depths as the spacing changes. As explained above in conjunction with FIG. 1d, the electrode pattern 52 on the dosimeter of FIG. 2b could be especially useful in monitoring the progression of surface charring of a part towards thermal, chemical or radiation degradation of the polymeric material or composite to a point where the part is compromise. Both FIGS. 2a and 2b show electrode pads 58 which make it easier to connect an impedance analyzer (not shown) to the dosimeter.

Figure 6A:
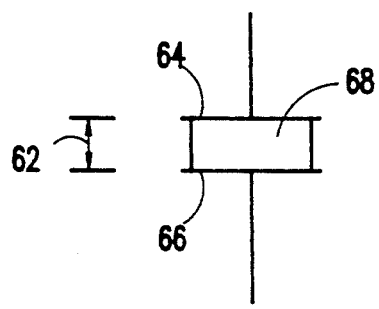
FIGS. 6a and 6b are side views of capacitors with spaced apart electrode plates which can be used in a manner analogous to that described in conjunction with the interdigitated designs shown in FIGS. 2a and 2b.
Figure 6B:
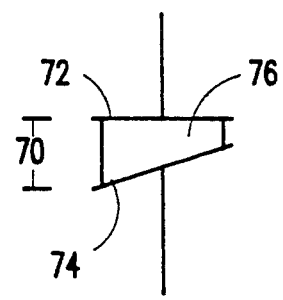

FIGS. 6a and 6b show capacitors with spaced apart electrode plates which can be used in a manner analogous to that described in conjunction with the interdigitated designs shown in FIGS. 2a and 2b. It is known that capacitance properties of interdigitated capacitor probes like those in FIGS. 2a and 2b can be roughly approximated by ordinary, spaced apart plate, capacitor designs. Variables to consider when using a capacitor with spaced apart plates include controlling the gap distance between the plates and controlling the ratio of the area contacted on the electrode plates to the volume of the material between the electrode plates. FIG. 6a shows one dosimeter design where the spacing 62 between the plates 64 and 66 is controlled to provide reproducible changes in $\epsilon'$ and/or $\epsilon''$ for material 68. FIG. 6b shows another dosimeter design where the spacing 70 between the plates 72 and 74 decreases across the surface of the material 76. The capacitor design of FIG. 6b would approximate the characteristics of the capacitors shown in FIG. 1d and FIG. 2b.

Figure 3:
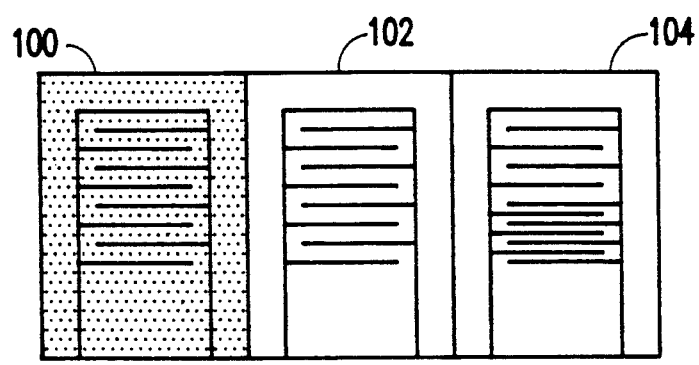
FIG. 3 is a top view of a dosimeter with an array of several different substrates.

For extended exposure time measurements, where many different times of exposure and/or the degree of degradation of several different use properties (strength modulus, elasticity, etc.) need to be monitored, the dosimeter would comprise an array of substrates. The materials chosen for the substrates, the thicknesses, the electrode patterns, and spacings would be varied so that each time interval and/or each structure/material use properties deterioration is detected through a significant, accurate, reproducible change in the magnitude and/or frequency dependence of $\epsilon'$, $\epsilon''$ and their equivalent circuit representations. Likewise, structures made from several different polymeric materials may be monitored using a dosimeter with an array of substrates, where each substrate may be a different material, have a different thickness, or have a different electrode geometry positioned thereon, and where each substrate in the array is matched to a particular use property of a particular material in the structure being monitored by the dosimeter. FIG. 3 shows an example of a dosimeter with an array of substrates 100, 102, and 104 which may be used for either extended exposure time measurements on a polymeric material or chemical fluid where each substrate monitors the deterioration of a different use property of the polymeric material or chemical fluid, or for monitoring a structure made from several different polymeric materials. Note that the substrate 100 can be different from substrates 102, and 104 (e.g., substrate 100 could be an epoxy while substrates 102 and 104 could by polyimides), the thicknesses (not shown) of the substrates 100, 102, and 104 could all be different and some of the substrates might be tapered as described above in conjunction with FIGS. 1a-d, and the spacing between the electrode lines on substrate 104 narrows as the spacing remains constant on substrates 100 and 102.

Preferably, the dosimeter could be on an isolated patch which is removable from a structure or part which is to be monitored. Alternatively, the dosimeter may be embedded permanently in the structure or part with electrical connection leads extending from the structure or part. A removable dosimeter would be expected to be the easiest to use and most cost effective arrangement. In operation, the dosimeter would be positioned adjacent to or on top of the structure or part and would be exposed to the same hostile environmental conditions as the structure or part. Periodically, or even continuously, complex permittivity data from the dosimeter would be assessed so that the use properties or physical attributes of interest for the structure or part could be determined. In a particular example where chemical fluids are being monitored, the dosimeter could be positioned on the end of dipstick like element which is positioned in the fluid during its use.

Figure 4:
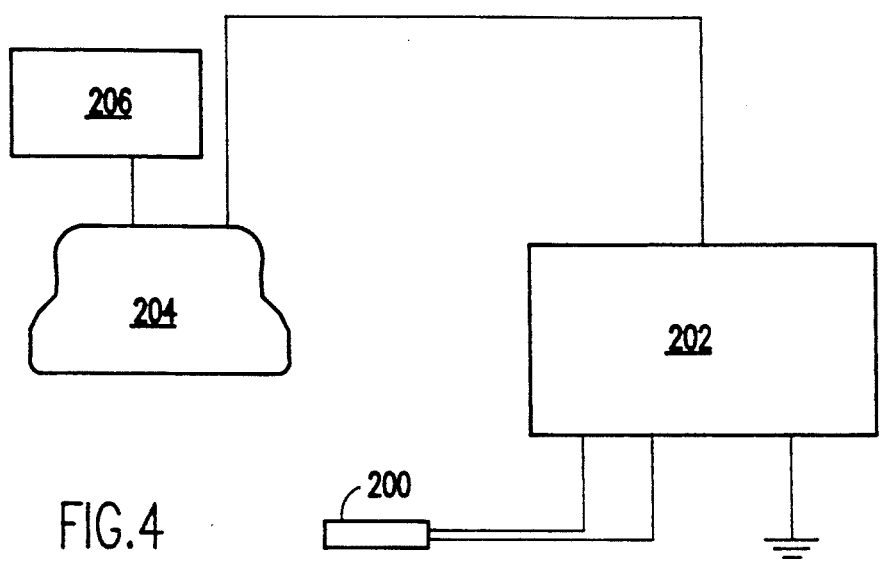
FIG. 4 is a schematic diagram showing a dosimeter connected to an impedance analyzer.

As shown in FIG. 4, the dosimeter 200 would be connected to an impedance analyzer 202 which is connected to a computer 204. As explained above, $\epsilon'$, $\epsilon''$, and their equivalent circuit representations (e.g., R,C; G,X; $|z|,\theta$; C,D; etc.) of the dosimeter 202 would be determined at one or several frequencies. Preferably several different frequencies would be monitored because the frequency dependence of $\epsilon'$ and $\epsilon''$, and their equivalent circuit representations can often be more sensitive than the magnitude of these complex permittivity values. An output device 206, such as a printer or display, will provide a technician with the measurement information for the dosimeter 202. The computer could be programmed to alert the technician that the use property or physical attribute of the structure, part, or chemical fluid is in need of repair or replacement based on the magnitude or frequency dependent measurements of $\epsilon'$ and/or $\epsilon''$. In fact, the rate of change and current value of $\epsilon'$ and/or $\epsilon''$ could be used to predict and warn of the pending replacement time.

The substrate material of the dosimeter will generally be in the family of materials from which a part or structure to be monitored is made (e.g., polyimides, epoxies, phenolics, silicate glass, etc.). The substrate material may even be the identical material of the part or structure to be monitored provided its $\Delta\epsilon$ and $\Delta M$, $\Delta K$, or other property of interest correlation, sensitivity and reproducibility is good or can be made to be good (e.g., combining with other substrates as in FIG. 1b or varying the geometry as in FIG. 1d and FIG. 6b, etc.). The substrate material may also be chosen because it has a known, reproducible degradation in the environment (radiation, oxidative, corrosive chemical) to which the structure being monitored is exposed. For example, polyvinylchloride (PVC) may be chosen as the substrate to monitor degradation of a structure that degrades with UV radiation even though the structure may be made from some other material such as a rubber product.

While the invention has been described in terms of its preferred embodiments, those skilled in the art will recognize that the invention can be practiced with modification within the spirit and scope of the appended claims.

Having thus described my invention, what I claim as new and desire to secure by Letters Patent is as follows:

1. A dosimeter which through reproducible changes in its complex permittivity, $\epsilon^*$, provides an indication of the properties of at least one of a polymeric material and a chemical fluid of interest, comprising:

a substrate;

an electrode pattern in the form of an interdigitated capacitor positioned on said substrate, at least one of said substrate and said electrode pattern being selected to yield reproducible changes in at least one of a real component, $\epsilon'$, and an imaginary component, $\epsilon''$, of a complex permittivity, $\epsilon^*$, or equivalent circuit representation thereof, for particular degradative conditions of interest, said reproducible changes being matched with a property of interest of said polymeric material or said chemical fluid to be monitored, wherein changes in at least one of $\epsilon'$ and $\epsilon''$, or equivalent circuit representations thereof, correspond with a degree of deterioration of said property of interest of said polymeric material or said chemical fluid to be monitored;

an impedance analyzer means connectable to said electrode pattern for detecting changes in at least one of $\epsilon'$ and $\epsilon''$, or equivalent circuit representation thereof, for said substrate at one or more frequencies; and a means for correlating detected changes in at least one of $\epsilon'$ and $\epsilon''$, or equivalent circuit representations thereof, with said degree of deterioration of said property of interest of said polymeric material or chemical fluid.

2. A dosimeter as recited in claim 1 wherein said substrate is selected from the group consisting of thermosets and thermoplastics.

3. A dosimeter as recited in claim 2 wherein said substrate is a thermoset selected from the group consisting of epoxies, polyamides, bismaleimides and polyimides.

4. A dosimeter as recited in claim 2 wherein said substrate is a thermoplastic selected from the group consisting of polyethers, polysulfones, and hydrocarbon or substituted polymer derivatives of ethylene.

5. A dosimeter as recited in claim 1 wherein said substrate has a geometry which is tapered relative to said electrode pattern.

6. A dosimeter as recited in claim 1 wherein said substrate is comprised of first and second materials that are positioned on first and second sides of said electrode pattern.

7. A dosimeter as recited in claim 1 wherein said electrode pattern has a uniform spacing between digits of said interdigitated capacitor.

8. A dosimeter as recited in claim 1 wherein said electrode pattern has a first spacing between digits at a first section on said substrate that is relatively larger than a second spacing between digits at a second section on said substrate.

9. A dosimeter which through reproducible changes in its complex permittivity, $\epsilon^*$, provides an indication of the properties of at least one of a polymeric material and a chemical fluid of interest, comprising:

an array of substrates;

electrode patterns in the form of an interdigitated capacitor positioned on each of said substrates, at least one of said substrates in said array and said electrode patterns on said substrates being selected to yield reproducible changes in at least one of a real component, $\epsilon'$, and an imaginary component, $\epsilon''$, of a complex permittivity, $\epsilon^*$, or equivalent circuit representation thereof, for particular degradative conditions of interest, said reproducible changes being matched with properties of interest of one or more polymeric materials or chemical fluids to be monitored, wherein changes in at least one of $\epsilon'$ and $\epsilon''$, or equivalent circuit representations thereof, correspond with a degree of deterioration of said properties of interest of said one or more polymeric materials or said chemical fluids to be monitored;

an impedance analyzer means connectable to said electrode patterns for detecting changes in at least one of $\epsilon'$ and $\epsilon''$, or equivalent circuit representations thereof, for each of said substrates at one or more frequencies; and a means for correlating detected changes in at least one of $\epsilon'$ and, or equivalent circuit representations thereof, with said degree of deterioration of said property of interest of said polymeric materials or said chemical fluids.

10. A dosimeter as recited in claim 9 wherein at least two of said substrates in said array are made from different materials.

11. A dosimeter which through reproducible changes in its complex permittivity, $\epsilon^*$, provides an indication of the properties of at least one of a polymeric material and a chemical fluid of interest, comprising:

a capacitor having a substrate positioned between a pair of spaced apart, electrode plates which has reproducible changes in at least one of a real component, $\epsilon'$, and an imaginary component, $\epsilon''$, of a complex permittivity, $\epsilon^*$, or equivalent circuit representation thereof, for particular degradative conditions of interest, said reproducible changes being matched with a property of interest of said polymeric material or chemical fluid to be monitored wherein changes in at least one of $\epsilon'$ and $\epsilon''$, or equivalent circuit representations thereof, correspond with a degree of deterioration of said property of interest of said polymeric material or said chemical fluid to be monitored;

an impedance analyzer means connectable to said spaced apart electrode plates of said capacitor for detecting changes in at least one of $\epsilon'$ and $\epsilon''$, or equivalent circuit representations thereof, for said substrate at one or more freequencies; and a means for correlating detected changes in at least one of $\epsilon'$ and $\epsilon''$, or equivalent circuit representations thereof, with said degree of deterioration of said property of interest of said polymeric material or said chemical fluid.

* * * * *